United States Patent [19]

Falk et al.

[11] Patent Number: 4,569,131

[45] Date of Patent: Feb. 11, 1986

[54] TOOL HAVING A HANDLE WITH AN INTERCHANGEABLE INSERT PORTION

[75] Inventors: Ernst Falk, Sternenfels-Diefenbach; Siegfried Hiltebrandt, Knittlingen; Johann Knoesel, Bretten, all of Fed. Rep. of Germany

[73] Assignee: Richard Wolf GmbH, Fed. Rep. of Germany

[21] Appl. No.: 582,790

[22] Filed: Feb. 23, 1984

[30] Foreign Application Priority Data

Jun. 1, 1983 [DE] Fed. Rep. of Germany ... 8316034[U]

[51] Int. Cl.[4] ............................................. B26B 13/00
[52] U.S. Cl. ...................................... 30/251; 30/262; 128/305; 128/751
[58] Field of Search ................. 30/212, 124, 250, 251, 30/261, 262; 294/19 R, 104; 128/321, 751, 305

[56] References Cited

U.S. PATENT DOCUMENTS

| 1,295,492 | 2/1919 | Heaton | 294/104 X |
| 3,964,468 | 6/1976 | Schulz | 128/751 |
| 4,254,549 | 3/1981 | McMullin | 30/251 |

Primary Examiner—Douglas D. Watts

[57] ABSTRACT

A tool having an insert portion mounted on a handle portion which handle portion will actuate a pincher-like tool arrangement on the free end of the insert portion characterized by a locking arrangement for holding the pincher-like tool in a closed position by holding the handle portion in the closed position and a stop arrangement to limit the amount of movement of the pincher-like tool toward the closed position.

7 Claims, 5 Drawing Figures

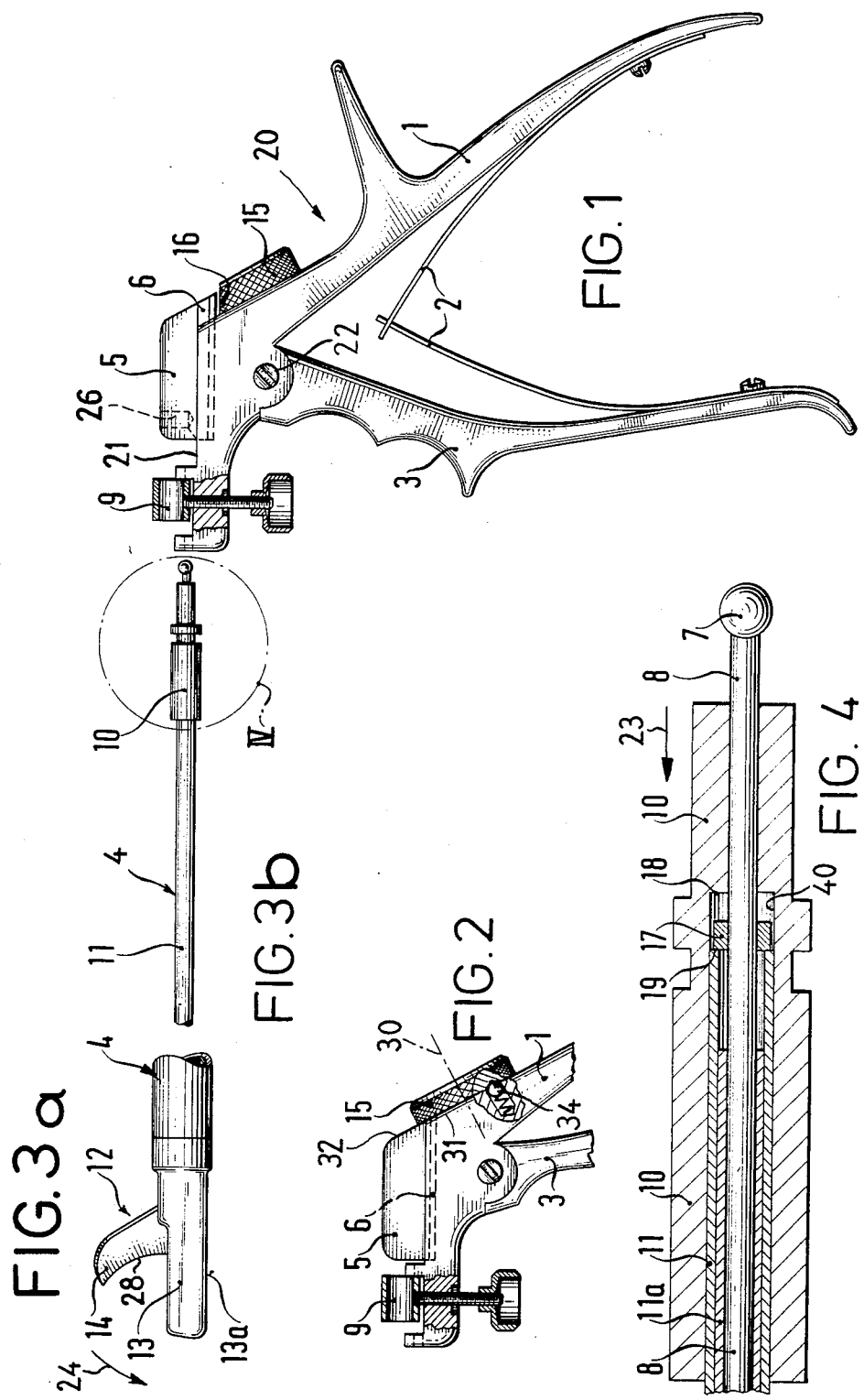

TOOL HAVING A HANDLE WITH AN INTERCHANGEABLE INSERT PORTION

BACKGROUND OF THE INVENTION

The present invention is directed to a tool having a handle and an insert portion, which has first and second ends with a pair of pivotally connected members at the first end to form a pincher-like tool for insertion into a body cavity. The members of the pincher-like tool are movable between an open-mouth position and a closed position with the members overlapping. The tool also includes an arrangement of an actuator rod received in a hollow support shaft for moving the members between the positions and the shaft is connected to one grip leg of a handle while the rod is coupled to a slidable carriage which is mounted to slide on the one grip leg and is moved by a second grip leg which is pivotally connected to the first leg for movement between an opened first position and a closed second position and is normally biased by a spring arrangement to the opened first position.

In order to prevent problems during insertion of the first end of the insert portion into a body cavity, the members that form the pincher-like tool must be held in a closed position during the step of insertion. This can be accomplished either by the physician gripping and holding the two handles in the closed second position against the force of the spring arrangement or by utilizing a trocar shield or shell. Since the two members forming the pincher-like tool may consist of a movable member and a stationary member or two movable members which are pivoted relative to one another, the movable member can be pivoted past a closed position so that an edge of each of the members extends past the other member. If the movable members are blades of a cutting instrument such as scissors, the movement past the closed position means that the cutting surfaces are exposed or projected past the protection of the adjacent member. Thus, injury to body organs or tissue can occur during insertion of the pincher-like tool into the body cavity. Also, the cutting edges of the blades can be damaged if the tool is inserted through some instrument channel or the like.

SUMMARY OF THE INVENTION

The present invention is directed to providing a tool which eliminates problems with fatigue and over-stressing of the physician while inserting the pincher-like tool into a body cavity. The invention also provides a tool which eliminates both the possibility of damaging of the members of the pincher-like tool due to being closed past the closed position and damaging the body cavity during insertion because of exposed sharp edges.

To accomplish this task, the invention is directed to an improvement in a tool having a handle and an insert portion, said insert portion having a first and second end with a pair of pivotally connected members at the first end to form a pincher-like tool for insertion into a body cavity, said members of the pincher tool being movable between an open-mouthed position and a closed position with the members overlapping, means for moving the members between said positions including an actuating rod received in a hollow support shaft, said handle having a first grip leg with a slidable carriage, a second grip leg being pivotally mounted on the first leg for movement between an opened first position and a closed second position and being connected to the carriage to move it on the first leg and resilient means for biasing the second leg to the first position, said tool having coupling means for exchangeably connecting the second end of the insert portion to the handle with the hollow shaft being connected to the first leg and the end of the rod being connected to the carriage so that when the second leg moves to the second position, the members of the pincher-like tool are moved to the closed position. The improvements include locking means for holding the second leg in the second position and stop means for limiting the amount of pivotal movement of the members in at least the direction toward the closed position said stop means comprising a stop on the actuating rod and at least one interior stop in the hollow shaft.

Preferably, the stop means includes two interior stops which are spaced apart to both limit the direction of movement toward the closed position and the angle of opening for the open-mouthed position. Preferably, the locking means includes an element engaging the slidable carriage to hold it and the second grip arm in the closed position.

Through the above improvements, a pincher-like tool can be closed by pressing the grip legs together against the resilient or spring means and then with the grip legs in the closed position, the element of the lock means can be shifted to engage the carrier to hold the legs in the closed position and to also hold the pivotal members in the closed position. Thus, the hand is unburdened during the step of insertion of the pincher-like tool into the body cavity and during removal of the pincher-like tool from the body cavity. In addition, the limit means which includes the stop on the actuating rod and the interior stop limit the pivotal movement of the member toward the closing position so that the members do not move so far to have sharp edges extending past the adjacent member by overshooting the closed position. Thus, the cutting edges on the members, if it is a scissors-type tool, do not become exposed to cut tissue during insertion of the insert portion into the body cavity. The other interior stop will limit the amount of opening of the two pivotal members forming the pincher-like tool after disengaging the locking means from the sliding carriage and will limit the angle of the aperture of the mouth being formed. If the stops are fixed, they allow the maximum angle for the mouth in the open-mouthed position and maximum closing of members. Thus, when the insert portion is used with different handles, the stops will usually be correct. It is also possible to provide means for adjusting the space between the interior stops. Thus, by adjusting one of the limit stops, such as the one that limits the amount of opening of the pivotal members, the angle can be adjusted. By providing each of the insert portions with the stop means, the pivotal members of the insert portion will not move past the desired closed position regardless of what handle portion they are used with.

Another feature is if the pivotal members act as a blade working on an anvil, then the stop means will prevent the application of excessive force to the cutting blade aqainst the anvil to prevent damage thereof even though the grip legs of the handles are squeezed beyond the closed position.

BRIEF DESCRIPTION OF THE DRAWINGS

FIG. 1 is a side view with portions broken away for purposes of illustration of the handle in the opened first position in accordance with the present invention;

FIG. 2 is a partial side view of the handles with portions broken away showing the handle in the closed second position;

FIG. 3a is an enlarged view of one end of the insert portion having the pivotal members forming the pincher-like tool;

FIG. 3b is a view of the second end of the insert portion of a scale similar to FIG. 1; and FIG. 4 is an enlarged cross-sectional view of the portion of the second end in the circle IV.

DESCRIPTION OF THE PREFERRED EMBODIMENTS

The principles of the present invention are particularly useful in a tool which has a handle generally indicated at 20 in FIG. 1 and an insert portion illustrated in FIGS. 3a and 3b. The handle 20 has a first grip leg 1 which can be considered as a stationary leg. An upper surface 21 of the leg 1 has a slidable carriage 5 which has a projection or track 6 received in a mating track of the grip leg 1. A second grip leg 3 is pivotally mounted at a pin or axle 22 on the first grip leg 1 and is movable between an open first position illustrated in FIG. 1 and a closed second position as illustrated in FIG. 2. To urge the second grip leg 3 to the first position, a resilient or spring means composed of a pair of springs 2 is mounted between the two grip legs 1 and 3.

The insert portion 4 at a first end illustrated in FIG. 3a has a pincher-like tool generally indicated at 12 which is formed by a pair of members 13 and 14 which are pivotally connected together for relative movement from the illustrated open-mouth position to a closed position wherein the member 14 is moved to a position overlapping the member 13. As illustrated, the member 13 is a stationary member which is rigidly connected to a hollow shaft 11 and the member 14 pivots relative to this member to a closed position. To cause the pivoting of the member 14, the hollow shaft 11 as illustrated in FIG. 4 has an actuator rod 8 which is connected to the member 14 and when the rod 8 is moved in the direction 23, the member 14 will pivot in the direction of the arrow 24 of FIG. 3a. The rod 8 terminates at the opposite end from its connection to the member 14 in a ball-shaped head 7. In addition, the hollow shaft 11 at the second end has a coupling part 10.

To connect the handle 20 to the insert portion 4, the first leg 1 has a tubular coupling part to receive the coupling part 10 and the ball-shaped head 7 is received in a groove or slot 26 in the carriage 5. Thus, movement of the leg 3 from the closed position of FIG. 2 to the open position illustrated in FIG. 1 will cause the rod 8 to move in a direction opposite to the arrow 23 to open the pincher-like tool 12. The tool with the handle 20 and the insert portion 4 as discussed up to now is a conventional tool known in the art. To operate the tool, the physician grasps the two leg portions 1 and 3 and squeezes them to the closed position of FIG. 2. The movement to the closed position moves the carriage 5 to a forward position to shift the actuating rod 8 in the direction of arrow 23 to cause the member 14 to pivot to a closed position which is overlapping the member 13. While in the closed position, the insert portion 4 can then be inserted into a body cavity either directly or through an instrument channel or the like. However, in the prior known devices the physician needed to continue to squeeze the grip legs 1 and 3 to the closed position. Also, if the handles were squeezed too far, it was possible that in some insert portions for the member 14 to be rotated too far in the direction of the arrow 24 so that a cutting edge 28 of the member 14 extends past a back edge 13a of the member 13 and would be exposed to damage tissue or to cut organs during the step of inserting.

The present invention overcomes these defects by providing lock means on the first grip leg 1. As illustrated, the lock means include a disk element or member 15, which is illustrated as being mounted for rotation about an axis 30. When the carriage 5 has been moved by the grip leg 3 to the forward position illustrated in FIG. 2, the disk element 15 is rotated and has a surface 31 engaging a back surface 32 of the carriage to hold it in this forward position even after release of pressure on the grip legs 1 and 3. The member 15 as illustrated in FIG. 1 has a cutout portion 16 so that when it is rotated to the position illustrated in FIG. 1 the surface 31 will disengage the back surface 32 of the carriage 5 and allow it to be moved to the open or rear position. As illustrated in FIG. 2, the two rotational positions of the member or element 15 can be fixed by means of a detent such as a spring-biased ball 34, which can be engaged in a depression in a back surface 31 of the disk 15. Thus, by providing depressions at two spaces, a rotation of 90° can be easily controlled by this detent.

In order to prevent the over-closing of the pivotal member 14 so its edge 28 extends past the edge 13a, stop means are provided to limit the amount of axial movement of the rod 8 in the shaft 11. As illustrated, the sleeve 11 has an insert 11a which provides a slidable seal for the rod 8 and also supports the rod 8 in the shaft 11 adjacent the coupling part 10. As illustrated in FIG. 4, the limit means includes an annular limit stop 17 which is a circumferential member on the rod 8 that extends between a stop 18 formed by a shoulder in the member 10 and a stop 19 which is formed by the end of the tube or shaft 11. In the position illustrated, the stop 19 has limited movement of the stop 17 and the rod 8 in the direction of the arrow 23 and thus the member 14 cannot be rotated to a position where the edge 28 extends beyond or past the edge 13a. In the illustrated embodiment, the stop 19 is positioned so that the two members 13 and 14 are in the desired overlapping superimposed positon when in the closed position. If the member 14 was a straight blade acting with the member 14 which was an anvil, then the stop 19 is positioned to stop the movement of the rod when the blade engages the anvil. If, as illustrated, the member 13 has a cutting blade, its cutting edge will not extend past the back edge of the member 14. Thus, the two cutting edges of the two members 13 and 14 when moved to the closed position do not project beyond the back edge such as 13a of the opposite member and they cannot lead to injury of organs or body tissue in the body cavity. The stop 18 will limit the amount of opening of the two members 13 and 14 by limiting the amount of movement of the rod 8 in the direction opposite to the arrow 23.

The spacing between the stops 18 and 19 can be fixed so that both the maximum allowable angle for the open-mouth position is obtained and the maximum movement in the direction of arrow 24 to the closed position is obtained. Thus, when using the insert portion with another handle, no adjustments are necessary.

It is also possible to replace the locking means which utilizes the rotary disk 15 by another locking mechanism, for example, a sliding element or the like. In other words, positioning a member in the position of the disk 15 to move from a retracted position such as illustrated in FIG. 1 to a position with a surface abutting the carriage surface 32 to prevent movement to the open position.

It is also advantageous to be able to adjust the spacing between the stops 18 and 19. This can be done by adjusting the amount of insertion of the hollow shaft 11 into a bore 40 of the coupling part 10. Another way is to form the coupling part 10 out of two parts which are threaded together. In this way, the distance between the two stops 18 and 19 can be changed by screwing the parts together or unscrewing the parts.

Although various minor modifications may be suggested by those versed in the art, it should be understood that we wish to embody within the scope of the patent granted hereon, all such modifications as reasonably and properly come within the scope of our contribution to the art.

We claim:

1. In a tool having a handle and an insert portion, said insert portion having first and second ends with a pair of pivotally connected members at the first end to form a pincher-like tool for insertion into a body cavity, said members of the pincher-like tool being movable between an open-mouthed position and a closed position with the members having overlapping edges, means for moving the members between said positions including an actuating rod received in a hollow support shaft, said handle having a first grip leg with a slidable carriage, a second grip leg being pivotally mounted on the first leg for movement between an opened first position and a closed second position and being connected to the carriage to move it on the first leg, and resilient means for biasing the second leg to the first position, said tool having coupling means for interchangeably connecting the second end of the insert portion to the handle with the hollow shaft connected to the first leg and the end of the rod connected to said carriage so that when the second leg moves to the second position the members of the pincher-like tool are moved to the closed position, the improvement comprising locking means having an element mounted on said first grip leg and movable for engaging the slidable carriage for immobilizing said carriage and thereby holding the second grip leg in the second position, and stop means for limiting the amount of pivotal movement of the members in both the direction toward the open-mouthed position and the direction toward the closed position, said stop means comprising a ring on the actuating rod disposed between a pair of spaced interior stop surfaces in the hollow shaft.

2. In a tool according to claim 1, wherein the element of the locking means has a cutout portion and is mounted for rotation on the first leg between an unlocking position with the cutout portion enabling movement of the carriage past the element to the rear position and a second position engaging a surface of the carriage to prevent movement to the rear position, and detent means for fixing the element in each of the said two rotational positions.

3. In a tool according to claim 2, wherein the hollow shaft terminates in a coupling part, and said interior stops are disposed on said coupling part with the distance therebetween being adjustable.

4. In a tool according to claim 3, wherein the pair of internal stops in the coupling part limit the maximum amount of opening of the pivotal members of the pincher-like tool and the maximum closing, said maximum being greater than the normal closing angle produced by the handle.

5. In a tool according to claim 4, wherein the hollow shaft includes a tubular insert for supporting the end of the actuating rod and to provide a seal around the actuating rod.

6. In a tool according to claim 1, wherein the second end of the hollow shaft has a coupling part, said internal stops being disposed therein.

7. In a tool according to claim 1, wherein the hollow shaft and has a tubular insert adjacent the second end for supporting the actuating rod and sealing in the shaft.

* * * * *